United States Patent [19]
Oddsson et al.

[11] Patent Number: 6,119,530
[45] Date of Patent: Sep. 19, 2000

[54] FORCE SENSING DEVICE

[75] Inventors: Lars I. E. Oddsson, Boston; Charles M. Cardoza, Merrimac, both of Mass.

[73] Assignee: Biomotions, Inc., Boston, Mass.

[21] Appl. No.: 09/036,750

[22] Filed: Mar. 9, 1998

(Under 37 CFR 1.47)

[51] Int. Cl.$^7$ ........................................ G01D 7/00
[52] U.S. Cl. ........................ 73/862.42; 73/862.43
[58] Field of Search ..................... 73/862.41, 862.42, 73/862.43, 862.46, 862.642

[56] References Cited

U.S. PATENT DOCUMENTS

| | | | |
|---|---|---|---|
| T934,002 | 5/1975 | Trail, Jr. | 73/862.42 |
| 4,448,083 | 5/1984 | Hayashi | 73/862.42 |
| 4,520,679 | 6/1985 | Hatamura | 73/862.42 |
| 5,315,882 | 5/1994 | Meyer et al. | 73/862.44 |
| 5,706,027 | 1/1998 | Hilton et al. | 345/156 |
| 5,821,432 | 10/1998 | Sidler et al. | 73/862.43 |

*Primary Examiner*—Max Noori
*Attorney, Agent, or Firm*—Howard & Howard

[57] ABSTRACT

A force sensing device for use in analyzing the movement of a person or animal. The device includes a base and a platform supported on the base by ball casters. The platform includes first and second plates with pneumatic tubing positioned between the plates. Forces on the platform result in compression of the pneumatic tubing, and the corresponding pressure changes in the pneumatic tubing are measured by associated pressure transducers. The device includes side rails which extend upwardly from the base and surround the platform. The side rails each include first and second plates with pneumatic tubing positioned between the plates. Side-to-side movement of the platform against the side rails results in compression of the pneumatic tubing in the side rails, and associated pressure transducers measure the corresponding pressure changes. The measurements from the pressure transducers are converted into force measurements and used to analyze the movement of the person or animal.

22 Claims, 2 Drawing Sheets

FORCE SENSING DEVICE

TECHNICAL FIELD

The subject invention generally relates to a force sensing device and, more specifically, a force-sensing device for use in analyzing the movement of a person or animal.

BACKGROUND ART

In various medical and sports-related fields, it is important to accurately measure the forces created by, or placed upon, a person or animal during walking, running, or other movement. This analysis is useful during physical therapy to detect problems in need of therapy and to monitor the progress of a patient. This analysis can also be used for measuring the intensity of exercise and effect of the exercise on a patient during physical therapy. Further, such analysis is useful to monitor the stride of an animal, such as a horse, during training of the animal. Force measuring devices have been developed as a tool to provide detailed, objective force measurements to assist in this type of movement analysis.

U.S. Pat. No. 4,195,643 to Pratt, Jr. discloses one example of a force measuring device which uses ceramic capacitors to detect forces applied in a vertical direction against the device. The ceramic capacitors produce an electrical signal representative of the forces applied thereto, and these signals are analyzed to study the motion of the person or animal on the device and gauge the physiological condition of the person or animal on the device. U.S. Pat. No. 5,005,140 to Havriluk discloses another force-measuring device which measures forces applied to fluid-filled tubes or containers by detecting pressure changes within the fluid containers. The fluid containers are, for example, attached to the foot of a person. As the person begins to walk, the pressure fluctuates in various regions of the fluid containers, and these pressure changes are detected by force transducers.

Unfortunately, the prior art force measuring devices are only adapted to measure forces in a single, generally vertical direction. The devices are not adapted to measure both vertical forces and shear forces applied by a person or animal, information which would be highly useful in a movement analysis.

SUMMARY OF THE INVENTION

The present invention provides a force measuring device comprising a platform and a member disposed adjacent the platform. A first force sensor is operatively engaged with the platform for detecting forces applied to the platform in a direction perpendicular to the platform, and a second force sensor is operatively engaged with the member for detecting forces applied by the platform to the member in a direction parallel to the platform.

The present invention also provides a force measuring device comprising a platform and a member disposed adjacent the platform. A first force sensor is operatively engaged with the platform for detecting forces applied to the platform in a direction perpendicular to the platform, and a second force sensor is disposed between the platform and the member for detecting relative forces between the platform and the member in a direction parallel to the platform.

By providing a force-measuring platform which includes sensors for measuring both perpendicular and parallel forces, more information can be provided for use in analyzing the movement of a person or animal.

DETAILED DESCRIPTION OF THE PREFERRED EMBODIMENTS

Figure 1:
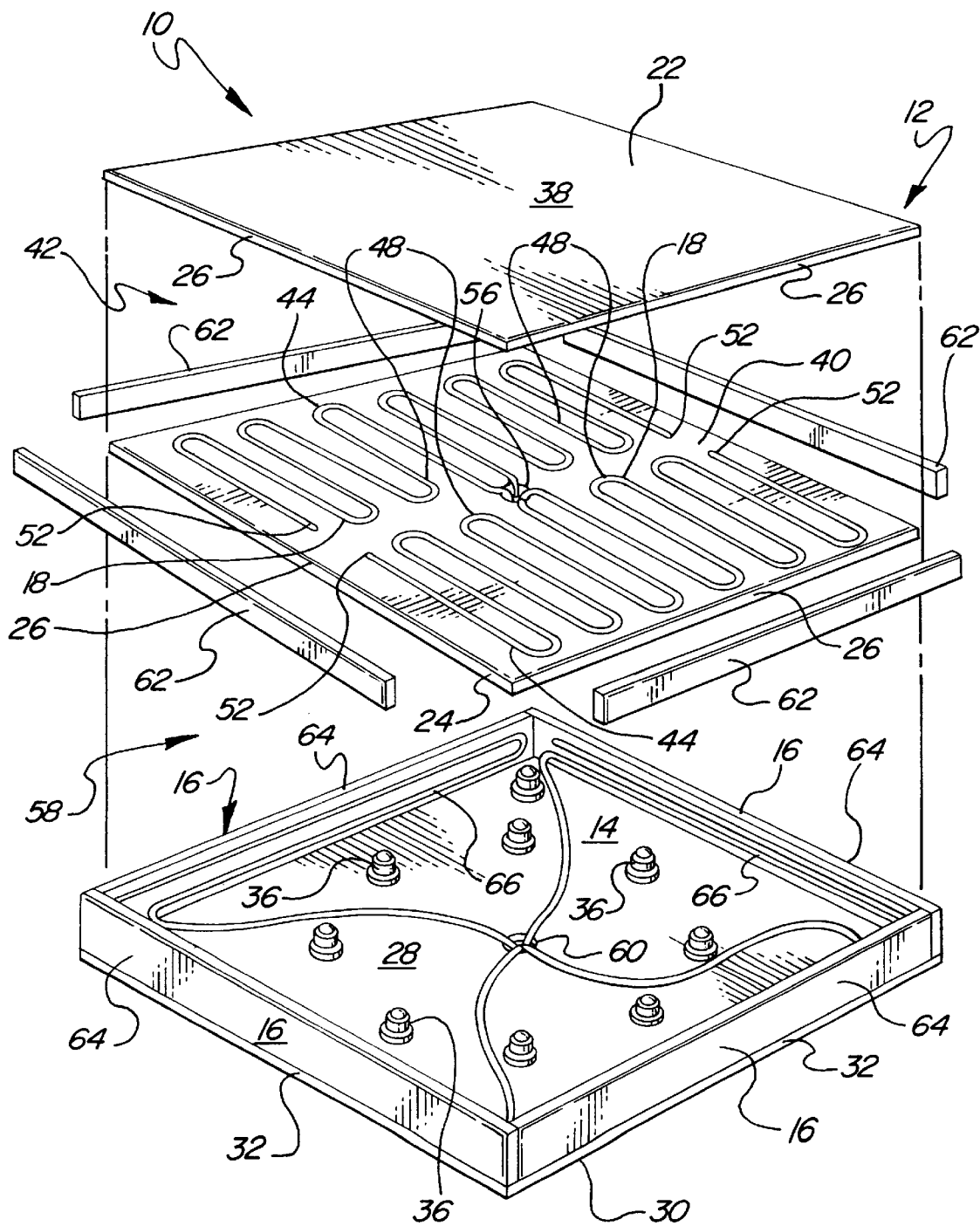
FIG. 1 illustrates an exploded perspective view of the force-measuring device of the present invention.
Figure 2:
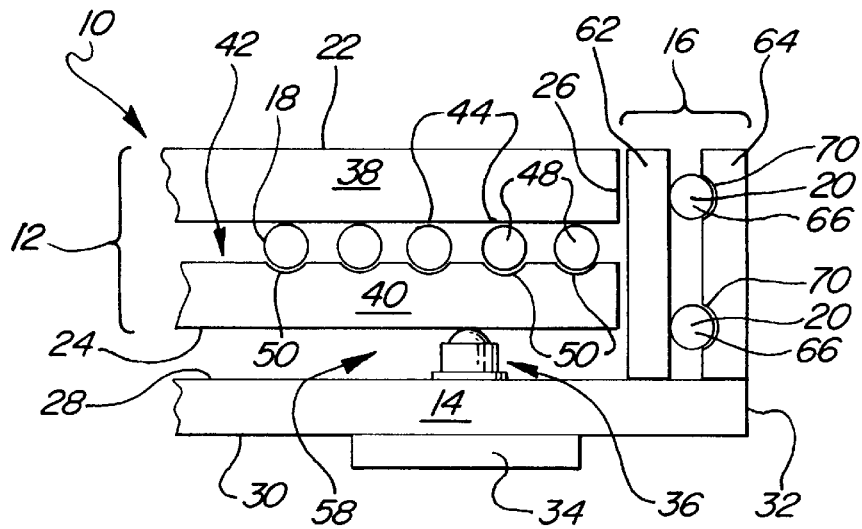
FIG. 2 illustrates a fragmentary cross-sectional view of the force measuring device of the present invention.

The present invention generally relates to a force-measuring device 10 for use in analyzing the movement of an animal or person who is stepping or walking on the device. As shown in FIGS. 1 and 2, the device 10 includes a platform 12 supported for lateral movement by a base 14. A plurality of side members 16 are fixed to the base 14 and extend upwardly therefrom adjacent the platform 12. As shown in the schematic representation of FIG. 3, a first force sensor 18 is operatively engaged with the platform 12 for detecting forces applied to the platform 12 in a direction perpendicular to the platform 12. A second force sensor 20 is operatively engaged with each side member 16 for detecting forces applied by the platform 12 to the side members 16 in a direction transverse to the platform 12.

As shown in FIGS. 1 and 2, the platform 12 comprises a rigid, flat, rectangular member having a top surface 22, a bottom surface 24, and four side edges 26. The platform 12 is preferably made of steel or another rigid metal, although plastic or other materials would certainly fall within the scope of the invention. The platform 12 also includes a traction-providing material (not shown) on the top surface 22 to prevent slipping by a person or animal stepping on the platform 12. The traction-providing material can comprise a rubber mat, strips of sandpaper-type material adhered to the platform 12, or other materials.

Similar to the platform 12, the base 14 comprises a rigid, flat, rectangular plate having a top surface 28, a bottom surface 30, and four side edges 32. The base 14 is also preferably made of the same material as the platform 12 such as rigid metal or plastic. As shown in FIG. 2, the base 14 includes a support member 34 at each corner for supporting the base 14 above the ground or other substrate.

As shown in FIGS. 1 and 2, a plurality of bearings 36 support the platform 12 several inches above the base 14 while maintaining the platform 12 parallel to the base 14. The bearings 36 preferably comprise ball casters which are evenly spaced about the base 14 in sufficient number to provide adequate support for the platform 12 and the weight of a person or animal standing thereon. The ball casters 36 permit the platform 12 to freely move in a parallel or side-to-side manner relative to the base 14. Said another way, the platform 12 and base 14 are allowed to move in parallel planes with respect to one another.

The platform 12 comprises first and second plates 38,40 with a space 42 between the plates 38,40. The first and second plates 38,40 can be free floating relative to one another or joined together, as long as relative vertical movement between the first and second plates 38,40 is permitted. The first force sensor 18, or a portion thereof, is disposed in the space 42 between the first and second plates 38,40 and detects vertical forces on the platform 12 which result in compression of the first and second plates 38,40. The first force sensor 18 includes a first fluid container 44 disposed between the first and second plates 38,40 and a first pressure sensor 46 (shown schematically in FIG. 3) operatively engaged with the first fluid container 44.

In the preferred embodiment, the first fluid container 44 comprises a silicone tube 48 filled with air. Preferably, four discrete tubes 48 are used, with each tube 48 being operatively associated with a separate pressure sensor 46. As shown in FIG. 1, each tube 48 is disposed in a discrete region between the first and second plates 38,40 of the platform 12, dividing the area into equally sized quadrants. The tubes 48 are placed in a sinusoidal or S-shaped pattern within each quadrant to sufficiently cover the surface area of each quadrant. Four separate force measurements will be provided from the four tubes 48 and their associated pressure sensors 46, and the measurements can be averaged or analyzed individually depending upon the particular application for which the force measuring device 10 is being used.

As shown best in FIG. 2, the platform 12 also includes a plurality of grooves 50 disposed in one or both of the first and second plates 38,40. The tubes 48 between the first and second plates 38,40 are disposed within the grooves 50 which serve to accurately position the tubes 48 during installation. After placement within the grooves 50, the tubes 48 can be adhered to the grooves 50 by any number of flexible adhesives, including silicone adhesive.

Figure 3:
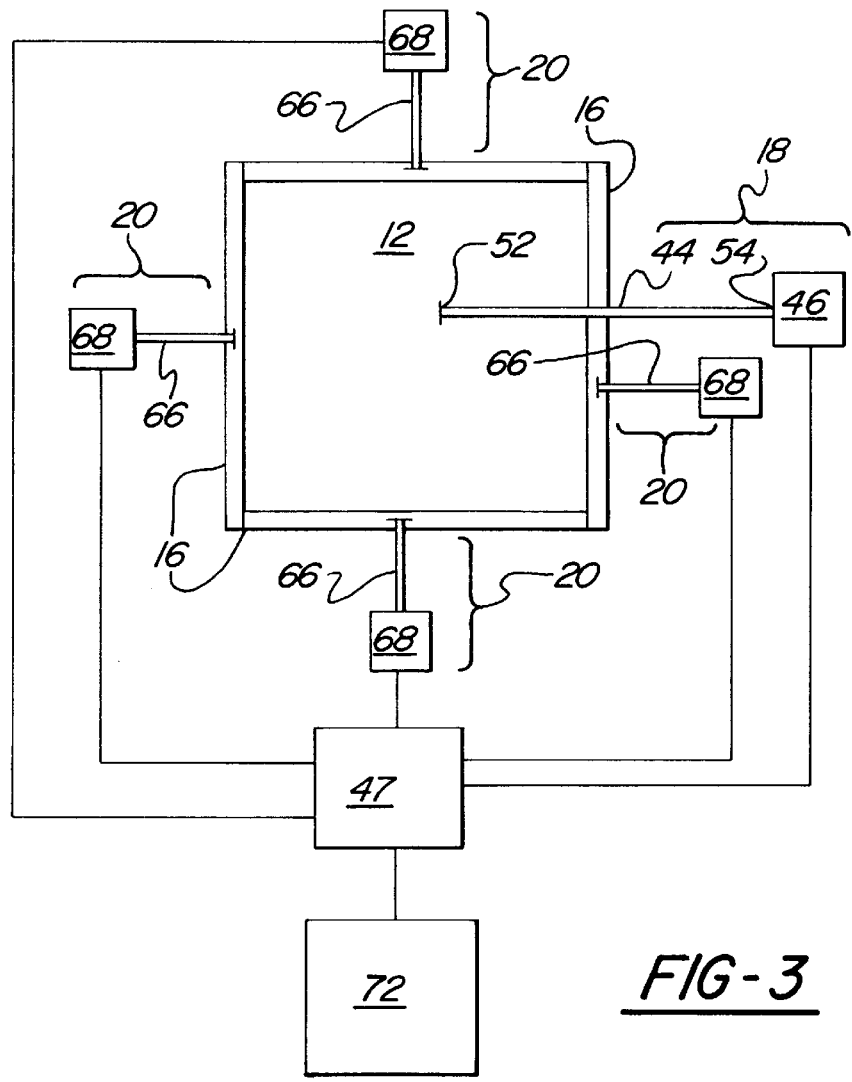
FIG. 3 illustrates a schematic representation of the platform and associated force sensors of the present invention.

As shown in FIG. 1, each fluid tube 48 includes a first, remote end 52 which is closed and a second end 54 which is operatively engaged with a pressure sensor 46 (shown in FIG. 3). FIG. 1 illustrates that the first end 52 of each tube 48 is disposed between the first and second plates 38,40, whereas the second end 54 extends through a small opening 56 in the center of the second plate 40 into the space 58 between the platform 12 and the base 14. The pressure sensor 46, as well as other electronics, can also be disposed within the space 58 between the platform 12 and the base 14. If the pressure sensor 46 is not disposed between the platform 12 and the base 14, the second end 54 of the fluid tube 48 will pass through an opening 60 in the base 14 into a region outside of the force measuring device 10.

As shown in FIGS. 1 and 2, the side members 16 each comprise a side rail including a front plate 62 and a back plate 64. The front plate 62 of each side member 16 is disposed adjacent a side edge 26 of the platform 12 and in contact therewith. Specifically, four side rails 16 are provided and surround each of the four side edges 26 of the platform 12. Both the front and back plate 62,64 of the side rails 16 are rectangular and formed of the same type of material as the platform 12 and base 14, such as rigid metal or plastic. Although the platform 12 and side rails 16 are in contact in a relatively snug fit, the platform 12 must be free to move both perpendicular to each side rail 16 and parallel to each side rail 16. Thus, the platform 12 and side rails 16 are not rigidly fixed together. Further, a bearing or similar low-friction joint (not shown) can be provided between the platform 12 and each side rail 16 to facilitate side-to-side motion between the platform 12 and each side rail 16. The bearing can comprise one or more ball casters or other types of rolling members to permit the desired relative movement.

Similar to the first force sensor 18, the second force sensor 20 also comprises an air-filled silicone tube 66 disposed between the front and back plates 62,64 of each side rail 16. In other words, four separate tubes 66 are provided with each tube 66 being operatively engaged with a separate pressure sensor 68, shown in FIG. 3. As shown in FIG. 2, the front and/or back plates 62,64 of each side rail 16 also include a groove 70 for positioning the tube 66 in the desired location. As shown in FIG. 1, the tube 66 extends in a U-shape about the majority of a peripheral edge of the front and back plates 62,64. The front and back plates 62,64 are secured together in the preferred embodiment with a flexible adhesive such as silicone adhesive which permits the front and back plates 62,64 to be compressed when a force is applied to the side rail 16.

In use, as a person or animal walks on the platform 12, vertical forces will be transferred through the platform 12 to the first force sensor 18. Specifically, vertical forces will compress the fluid tubes 48, increasing the pressure therein which is detected by the first pressure sensor 46. Similarly, shear forces placed on the platform 12 will press the platform 12 against one or more of the side rails 16, compressing the front and back plates 62,64 of the contacted side rails 16. The compression will increase the pressure within the fluid tubes 66 between the front and back plates 62,64, and the associated pressure sensor 68 will measure the pressure change. As represented in FIG. 3, an analog-to-digital converter 47 will translate the signals from the pressure sensors 46,68 into electrical signals which are representative of the vertical and shear forces applied to the platform 12. The signals can then be analyzed and interpreted by a computer 72.

The pressure sensors 46,68 of both the first force sensor 18 and the second force sensor 20 comprise any type of standard pressure sensor, such as those manufactured by Motorola Corporation having a 0–20 p.s.i. sensitivity. Any type of analog-to-digital converter 47 may be used with the present invention. Further, any type of personal computer 72, with the appropriate software, can be used to analyze and interpret the signals from the analog-to-digital converter 47. The particular type of computer and/or analog-to-digital converter is not important for carrying out this invention as would be understood by those skilled in the art.

Various other embodiments of the force-measuring device than that shown in the drawings would also fall within the scope of the invention. For example, a fluid container could be disposed directly between the platform 12 and the side rails 16 wherein the fluid container would be compressed directly by the platform 12. Further, shear forces applied to the platform 12 could be measured by a strain gauge or other device which would measure the relative, parallel forces between the platform 12 and the base 14, or between the platform 12 and the side rails 16.

It is also to be understood that although the invention is described in terms of measuring forces perpendicular to the platform 12 and/or parallel to the platform 12, the force sensors 18,20 could measure forces in any direction and then the forces in the desired direction could be calculated using a simple mathematical calculation.

Although the description of this invention has been given with reference to a particular embodiment, it is not to be construed within a limiting sense. Many variations and modifications will no doubt occur to those skilled in the art. For a definition of the invention, reference is made to the appended claims.

What is claimed is:

1. A force measuring device comprising:

a platform;

a first force sensor operatively engaged with said platform for detecting forces applied to said platform in a direction perpendicular to said platform, said first force sensor including a first fluid container and a first pressure sensor operatively engaged with said first fluid container;

a member disposed adjacent said platform; and a second force sensor operatively engaged with said member for detecting forces applied by said platform to said member in a direction parallel to said platform.

2. The force measuring device of claim 1 further including a base wherein said platform is supported by said base for lateral movement relative to said base.

3. The force measuring device of claim 2 wherein:

said platform includes first and second plates; and said first fluid container disposed between said first and said second plates of said platform.

4. The force measuring device of claim 2 wherein:

said member comprises a side rail including a front plate and a back plate;

said platform includes a top surface, a bottom surface, and an edge; and said front plate is disposed adjacent said edge of said platform.

5. The force measuring device of claim 4 wherein:

said second force sensor includes a second fluid container disposed between said front plate and said back plate of said side rail; and said second force sensor includes a second pressure sensor operatively engaged with said second fluid container.

6. The force measuring device of claim 3 wherein said first fluid container comprises tubing filled with air.

7. The force measuring device of claim 5 wherein said second fluid container comprises tubing filled with air.

8. A force measuring device comprising:

a platform;

a base supporting said platform for lateral movement of said platform relative to said base;

a bearing disposed between said base and said platform;

a first force sensor operatively engaged with said platform for detecting forces applied to said platform in a direction perpendicular to said platform;

a member disposed adjacent said platform; and a second force sensor operatively engaged with said member for detecting forces applied by said platform to said member in a direction parallel to said platform.

9. The force measuring device of claim 8 wherein said bearing comprises a ball caster disposed between said base and said platform.

10. The force measuring device of claim 3 wherein:

said first fluid container includes a plurality of air-filled tubes, each tube being operatively engaged with a separate pressure sensor; and each fluid-filled tube is disposed in a distinct region between said first and said second plates of said platform.

11. The force measuring device of claim 6 further including a sinusoidal groove disposed within said base wherein said tubing is disposed within said groove.

12. The force measuring device of claim 7 further including a groove disposed in said back plate of said side rail wherein said tubing is disposed within said groove.

13. The force measuring device of claim 4 wherein said side rail is fixed to said base.

14. A force measuring device comprising:

a platform;

a first force sensor operatively engaged with said platform for detecting forces applied to said platform in a direction perpendicular to said platform, said first force sensor including a first fluid container and a first pressure sensor operatively engaged with said first fluid container;

a member disposed adjacent said platform; and a second force sensor disposed between said platform and said member for detecting relative forces between said platform and said member in a direction parallel to said platform.

15. The force measuring device of claim 14 further including:

a base wherein said platform is supported by said base for lateral movement relative to said base.

16. The force measuring device of claim 15 wherein:

said platform includes a first plate and a second plate;

said first fluid container disposed between said first and second plates of said platform.

17. The force measuring device of claim 15 wherein:

said platform includes a top surface, a bottom surface, and an edge; and said member comprises a side rail disposed adjacent said edge of said platform.

18. The force measuring device of claim 17 wherein:

said second force sensor includes a second fluid container in contact with said side rail; and said second force sensor includes a second pressure sensor operatively engaged with said second fluid container.

19. The force measuring device of claim 15 further including a bearing disposed between said base and said platform.

20. The force measuring device of claim 17 wherein said side rail is fixed to said base.

21. A force measuring device comprising:

a platform;

a first force sensor operatively engaged with said platform for detecting forces applied to said platform in a direction perpendicular to said platform;

a member disposed adjacent said platform; and a second force sensor operatively engaged with said member for detecting forces applied by said platform to said member in a direction parallel to said platform, said second force sensor including a second fluid container disposed between said front plate and said back plate of said side rail and said second force sensor includes a second pressure sensor operatively engaged with said second fluid container.

22. The force measuring device of claim 21 wherein:

said first force sensor includes a first fluid container; and said first force sensor includes a first pressure sensor operatively engaged with said first fluid container.

* * * * *

UNITED STATES PATENT AND TRADEMARK OFFICE
CERTIFICATE OF CORRECTION

PATENT NO.   : 6,119,530
DATED        : September 19, 2000
INVENTOR(S)  : Oddsson, et al.

It is certified that error appears in the above-identified patent and that said Letters Patent is hereby corrected as shown below:

IN THE CLAIMS 21. (Amended). A force measuring device comprising:
   a platform;
   [a first force sensor operatively engaged with said platform for detecting forces applied to said platform in a direction perpendicular to said platform;]
   a member disposed adjacent said platform;[and]
   a [second] first force sensor operatively engaged with said member for detecting forces applied by said platform to said member in a direction transverse to said platform, said [second] first force sensor including a [second] first fluid container [disposed between said front plate and said back plate of said side rail] and said [second] first force sensor includes a [second] first pressure sensor operatively engaged with said [second] first fluid container; and a second force sensor operatively engaged with said platform for detecting forces applied to said platform in a direction perpendicular to said platform.

22. (Amended). The force measuring device of Claim 21 wherein:
   said [first] second force sensor includes a [first] second fluid container; and
   said [first] second force sensor includes a [first] second pressure sensor operatively engaged with said [first] second fluid container.

Signed and Sealed this

Third Day of July, 2001

*Attest:*

*Attesting Officer*

NICHOLAS P. GODICI
*Acting Director of the United States Patent and Trademark Office*